US006847913B2

United States Patent
Wigley et al.

(10) Patent No.: US 6,847,913 B2
(45) Date of Patent: Jan. 25, 2005

(54) AMBULATORY SURFACE SKIN TEMPERATURE MONITOR

(75) Inventors: Fredrick M. Wigley, Baltimore, MD (US); Robert A. Wise, Baltimore, MD (US); Paul D. Schwartz, Arnold, MD (US); Ark L. Lew, Ellicott City, MD (US); David D. Scott, Columbia, MD (US); Binh Q. Le, Vienna, VA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/264,442

(22) Filed: Oct. 4, 2002

(65) Prior Publication Data

US 2003/0069714 A1 Apr. 10, 2003

Related U.S. Application Data

(60) Provisional application No. 60/327,213, filed on Oct. 4, 2001.

(51) Int. Cl.$^7$ ............................................. G01K 13/00
(52) U.S. Cl. .................. 702/131; 600/349; 600/549; 374/100; 374/101; 374/109
(58) Field of Search .......................... 702/131; 300/300, 300/549; 374/100, 101, 109; 600/300, 549

(56) References Cited

U.S. PATENT DOCUMENTS

| 3,949,388 A | * | 4/1976 | Fuller ..................... 340/870.17 |
| 4,129,125 A | | 12/1978 | Lester et al. ........... 128/2.05 R |
| 4,306,569 A | * | 12/1981 | Weil et al. .................. 600/549 |
| 4,723,554 A | | 2/1988 | Oman et al. ................. 128/664 |
| 5,050,612 A | * | 9/1991 | Matsumura .................. 600/483 |
| 5,844,862 A | | 12/1998 | Cocatrre-Zilgien .......... 368/10 |
| 5,964,701 A | | 10/1999 | Asada et al. ................. 600/300 |
| 6,067,468 A | * | 5/2000 | Korenman et al. .......... 600/547 |
| 6,090,050 A | | 7/2000 | Constantinides ............ 600/549 |
| 6,198,394 B1 | * | 3/2001 | Jacobsen et al. ......... 340/573.1 |
| 6,315,719 B1 | * | 11/2001 | Rode et al. .................. 600/300 |
| 6,325,763 B1 | | 12/2001 | Pfeiffer et al. .............. 600/549 |
| 6,402,690 B1 | | 6/2002 | Rhee et al. .................. 600/300 |
| 6,416,471 B1 | | 7/2002 | Kumar et al. ................ 600/300 |
| 6,547,745 B1 | * | 4/2003 | Rubinstein ................... 600/549 |
| 2001/0044588 A1 | | 11/2001 | Mault .......................... 600/549 |
| 2001/0046471 A1 | | 11/2001 | Marek et al. ................. 424/9.1 |
| 2002/0019586 A1 | | 2/2002 | Teller et al. ................. 600/300 |

* cited by examiner

*Primary Examiner*—John Barlow
*Assistant Examiner*—Anthony T. Dougherty
(74) *Attorney, Agent, or Firm*—Francis A. Cooch

(57) ABSTRACT

An ambulatory skin temperature monitoring system. A flexible band is attachable to a patient. The flexible band also secures an electronics assembly that comprises the various electrical components that monitor and operate the ambulatory skin temperature monitoring system. At least one skin temperature sensor is positioned so that it is in contact with the patients skin when the system is attached to the patient. There is also an ambient temperature sensor positioned on the top surface of the electronics assembly housing for measuring and contrasting the ambient temperature to the skin temperature. The electronics assembly positioned within generally comprises a power source and a micro-controller. The micro-controller is coupled with the skin temperature sensor and the ambient temperature sensor. The micro-controller also includes a memory unit for storing temperature data obtained from the skin temperature sensor and the ambient temperature sensor. Data from the system can be downloaded to a remote computing device where software can plot the data in a desired format for analysis by medical personnel.

24 Claims, 3 Drawing Sheets

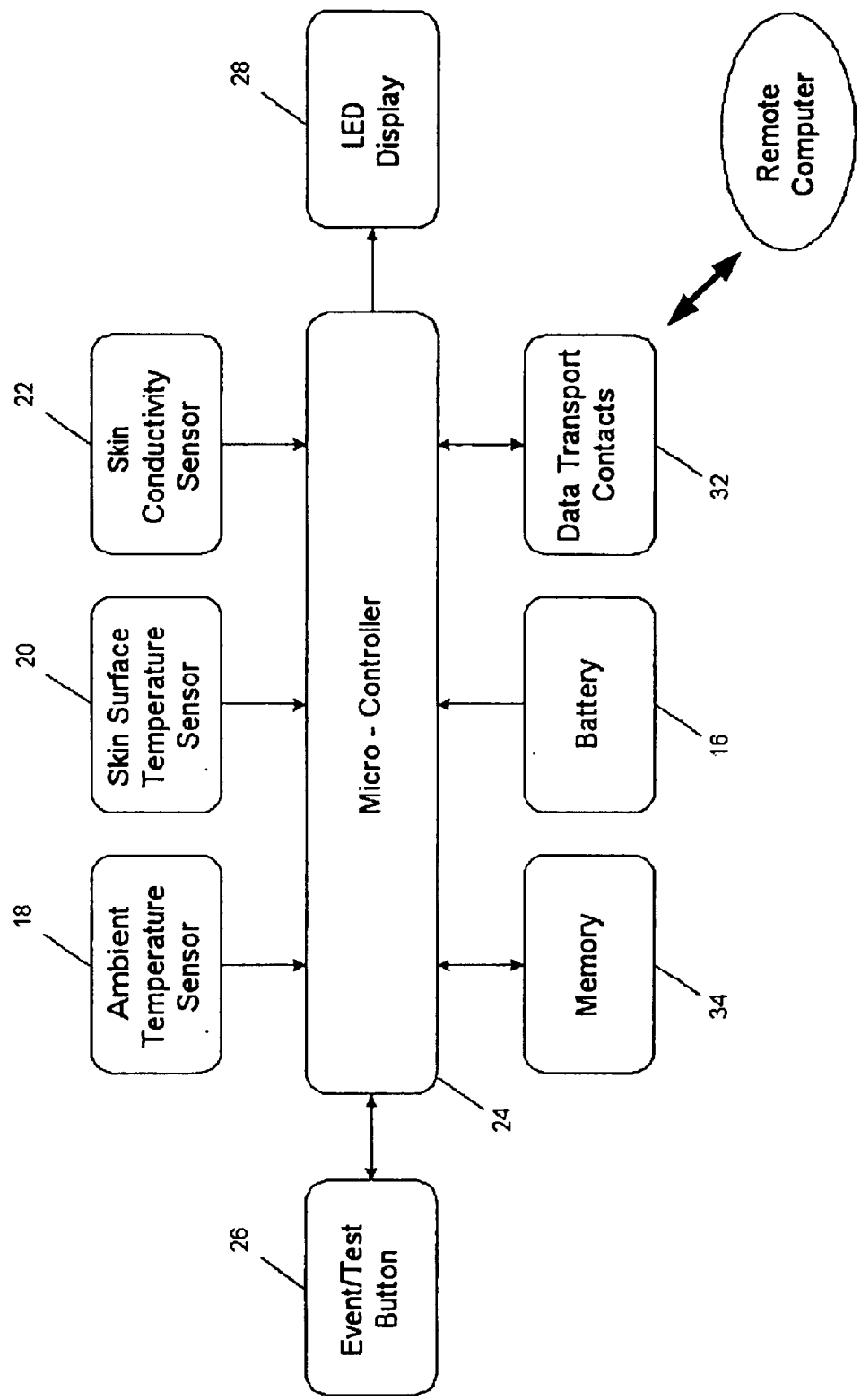

AMBULATORY SURFACE SKIN TEMPERATURE MONITOR

CROSS REFERENCE TO RELATED APPLICATIONS

This application is related to and claims the benefit of U.S. Provisional Patent Application Ser. No. 60/327,213, filed Oct. 4, 2001.

FIELD OF THE INVENTION

The present invention is related to a system and method for objectively monitoring surface skin temperature to assist in the treatment of medical disorders characterized by decreased blood flow to the extremities.

BACKGROUND

Raynaud's phenomenon patients experience episodic attacks that cause the blood vessels in the fingers and toes to constrict, limiting blood flow to the extremities, and potentially leading to permanent loss of function. During attacks, which are triggered in response to exposure to a cold environment, insufficient digital surface tissue blood flow may cause patients to experience skin color changes, numbness, and cold fingers and toes. Treatments are intended to reduce the number and severity of episodic attacks, and to prevent permanent damage. Raynaud's phenomenon attacks affect approximately five to ten percent of the population in the United States.

Traditionally, treatments are subjectively evaluated by asking patients to estimate the frequency and severity of Raynaud's attacks. Since each patient's subjective interpretation of an attack can vary widely, determining the efficacy of a particular treatment is problematic.

What is needed is a method for measuring surface skin temperature, as an indication of digital blood flow, in an ambulatory setting that will provide an objective indication of treatment efficacy during clinical trials, and provide valuable information during a drug approval process, for instance.

SUMMARY

The present invention is comprised of a miniaturized, programmable, stand-alone device that measures, records, and processes finger surface skin temperature and ambient temperature. The present invention can be used to aid in evaluating candidate treatments for Raynaud's phenomenon. Raynaud's phenomenon is but one application suitable for the present invention. The ambulatory monitor will be a small, simple, easily removable, non-obstructive device that will attach to the finger in a "band-aid" like manner and will permit recording and time-tagging critical evaluation data without restricting patient motion or activities. Since the ambulatory monitor is a self-contained data recorder, it will not require patient companion equipment (e.g. a portable data recorder or personal computer). The ambulatory monitor can be constructed to cover only a small portion of a patient's finger to minimize impact on digital blood flow and surface temperature.

The ambulatory monitor continuously samples temperature data periodically and records the temperature data directly in a memory contained within the ambulatory monitor electronics. The ambulatory monitor memory is typically non-volatile, so that recorded data will be retained even if ambulatory monitor power is unexpectedly interrupted. When the ambulatory monitor is removed (for patient washing, bathing, etc.) a built-in detector will automatically record the event time.

Data can be downloaded from the ambulatory monitor to a computing device such as, but not limited to, a PC or PDA. Raw data can be displayed and plotted for episodic events using customized or commercial-off-the-shelf (COTS) software programs.

In accordance with a first embodiment of the present invention, there is disclosed an ambulatory skin temperature monitoring system. A flexible band is attachable to a patient. The flexible band also secures an electronics assembly that comprises the various electrical components that monitor and operate the ambulatory skin temperature monitoring system. The housing includes a top surface and a bottom surface, wherein said bottom surface contacts with the skin of the patient when the flexible band is attached to the patient.

At least one skin temperature sensor is positioned so that it is in contact with the patients skin when the system is attached to the patient. There is also an ambient temperature sensor positioned on the top surface of the electronics assembly housing for measuring and contrasting the ambient temperature to the skin temperature. The electronics assembly positioned within generally comprises a power source and a micro-controller. The micro-controller is coupled with the skin temperature sensor and the ambient temperature sensor. The micro-controller also includes a memory unit for storing temperature data obtained from the skin temperature sensor and the ambient temperature sensor.

A skin conductivity sensor may also be attached to the housing and coupled with the micro-controller. The skin conductivity sensor provides feedback indicating whether the system is properly attached to the patient.

BRIEF DESCRIPTION OF THE DRAWINGS

FIG. 4 illustrates a block diagram of the functional processes of the ambulatory monitor.

DETAILED DESCRIPTION

The following figures use like reference numbers to represent like elements throughout the description.

Figure 1:
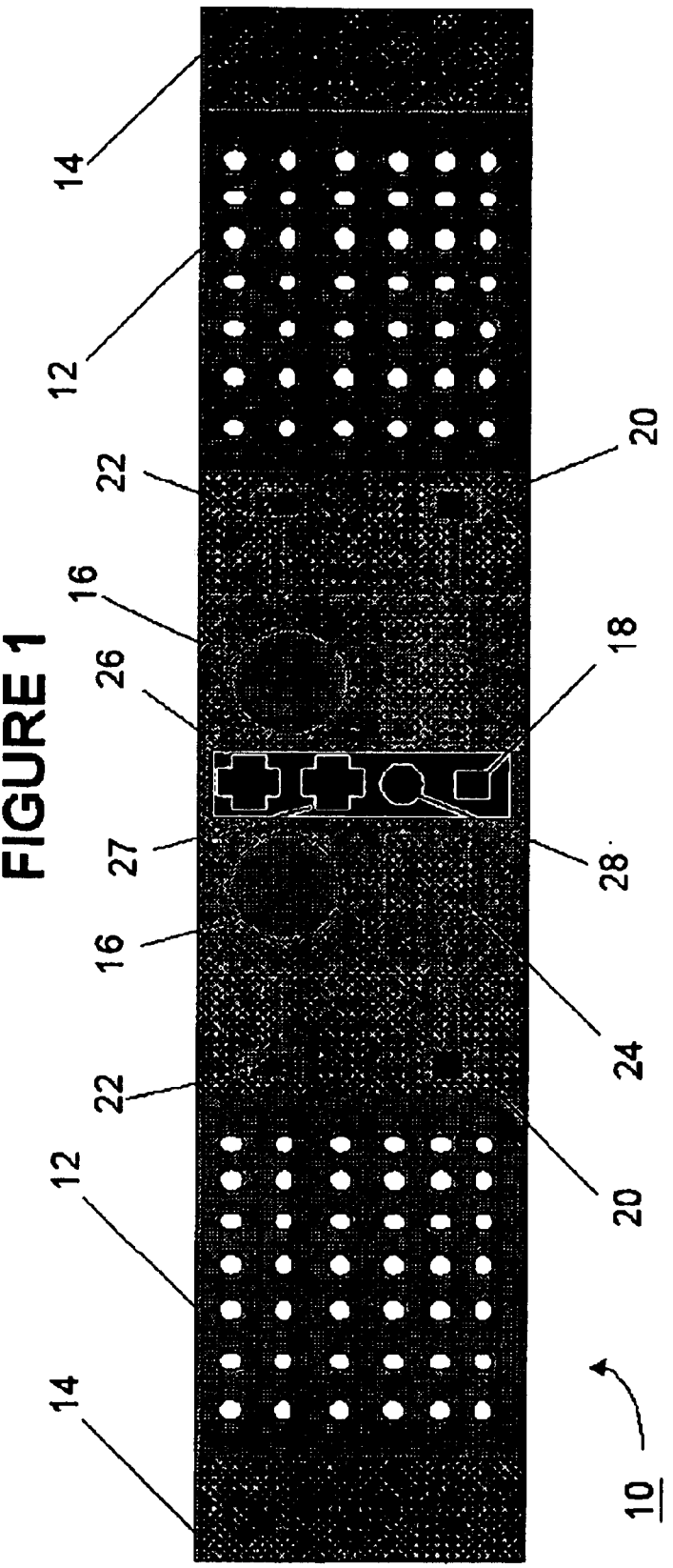
FIG. 1 illustrates a top view of the ambulatory monitor.
Figure 2:
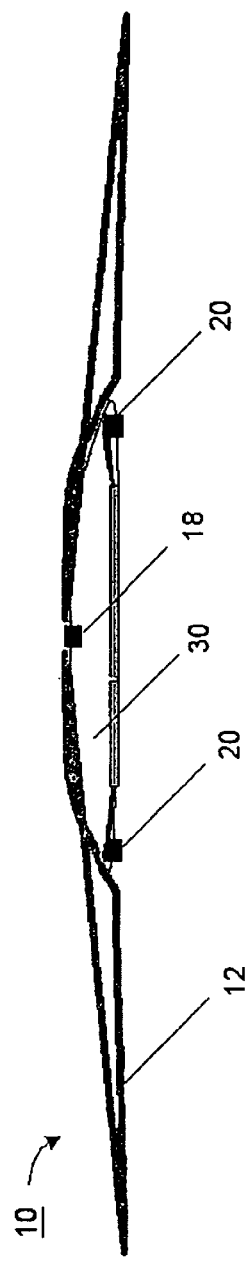
FIG. 2 illustrates a side view of the ambulatory monitor.
Figure 3:
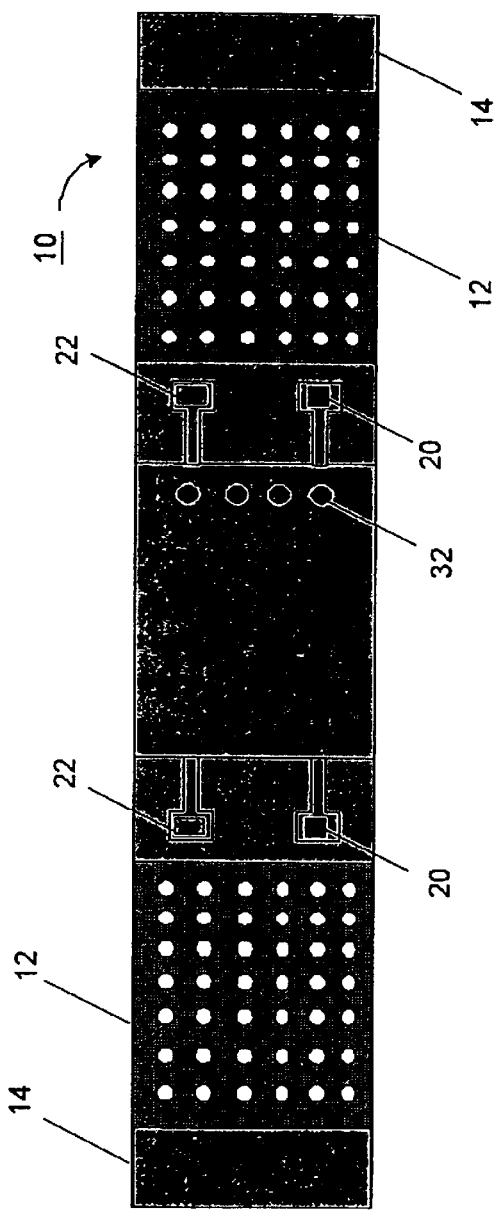
FIG. 3 illustrates a bottom view of the ambulatory monitor.

FIGS. 1–3 illustrate top, side, and bottom views of the ambulatory monitor respectively. The ambulatory monitor 10 is generally shaped like a typical band-aid bandage. The basic structure is comprised of an electronics section surrounded by a perforated flexible band 12 that includes a replaceable adhesive backing 14 on each end. The ambulatory monitor 10 is designed to be wrapped around a patient's finger and adhesively secured in place. The electronics portion of the ambulatory monitor 10 is comprised of a small battery 16, an ambient temperature sensor 18, one or more surface skin temperature sensors 20 (thermistors), one or more skin conductivity sensors 22, a micro-controller 24, an event/test button 26, a power readout button 27, and an LED 28 for providing visual feedback to a patient. The micro-controller 24 further includes a resident non-volatile memory device (not shown). The memory device stores skin temperature, skin conductivity, and event data obtained by the ambulatory monitor 10.

The electronics are potted with silicone or equivalent material to provide protection for the assembly and comfort for the patient 30. The electronics assembly forms a small (approximately 0.5 in. square) flat surface that can attach to the finger. A perforated flexible band 12 with its replaceable adhesive backing 14 secures the ambulatory monitor 10 to the finger without impacting blood flow or surface temperature. The adhesive backing 14 can be easily replaced whenever there is a need to remove the ambulatory monitor 10 from the patient's finger.

Also included in the ambulatory monitor 10 are data transport contacts 32 for downloading data from the memory device within the micro-controller 24 to a remote computing device where the data can be processed and displayed to medical personnel for analysis. The data transport contacts 32 can be accessed using appropriate computer technology such as, for instance, a serial I/O cable. Or, the data transport mechanism between the ambulatory monitor 10 and the remote computer can be a suitable wireless link. Power readout button 27 provides external power to the ambulatory monitor 10 for data transport purposes in the event that the batteries 16 have drained.

The batteries 16 provide electrical power to the ultra-low power, mixed signal micro-controller 24 that is connected to all of the electronics required to sample, time-tag, store, process, and download data. A pair of silver oxide battery cells, for instance, can provide power to operate the ambulatory monitor 10 for at least one month. The micro-controller 24 has low power operating modes that reduce its average power drain to a few microamperes. Skin surface temperature data is obtained from the thermistors 20 mounted beneath the perforated flexible strap 12. Ambient temperature data is obtained from a thermistor 18 mounted on top of the electronics board.

Skin conductivity sensors 22 serve two functions. The primary function of the skin conductivity sensors 22 is to ensure that the ambulatory monitor 10 is properly installed. The skin conductivity sensors 22 also serve as a crude indicator of the patient's emotional state. This is important because under some conditions, Raynaud's Phenomenon events are more likely to occur when patients are under emotional stress. The skin conductivity sensors operate by using the resistance between two metallic contacts to form a voltage divider with a fixed resistor.

FIG. 4 illustrates a block diagram of the functional processes of the ambulatory monitor. The micro-controller 24 acts as a centralized coordinating unit powered by battery 16 that manages the functions and data with respect to the ambulatory monitor 10. All of the sensors (ambient temperature 18, skin surface temperature 20, and skin conductivity 22) are coupled with the micro-controller 24 such that data gathered by these sensors is passed to the micro-controller. In addition, the micro-controller can be programmed to periodically poll the sensors for instantaneous temperature readings. The data sent from the sensors 18, 20, 22 to the micro-controller is stored in a memory device 34 that is part of micro-controller 24 itself. The event/test button 26 allows the patient to test the ambulatory monitor 10 and to record a suspected event. To test the ambulatory monitor 10, the patient depresses the event/test button 26 once. If either of the skin conductivity sensors 22 report measurements that are within an expected range, then the LED 28 will flash once for about a second. This indicates that the ambulatory monitor 10 is properly installed and ready for use. To record a suspected event (e.g., a Raynaud's event), the patient depresses the event/test button 26 twice. The LED 28 will flash once following the first depression and twice following the second depression. This confirms that the ambulatory monitor 10 has logged that a Raynaud's event is in progress according to the patient.

The ambulatory monitor 10 serves generally to gather temperature data from a patient's skin surface and from the ambient environment. The temperature data is then stored on-board the ambulatory monitor 10 where it is subsequently downloaded (either by cable or wirelessly) to a separate computing device. The separate computing device can then act on the data received. Software customized to interpret and plot the data can be utilized to display the data in a format that is of value to medical personnel. The medical personnel can then draw objective conclusions based on the temperature readings presented.

Such a system is very advantageous in evaluating the efficacy of treatments for Raynaud's phenomenon. Other medical conditions can benefit from the data gathered by the present invention. For instance, the ambulatory skin temperature data can be used in the monitoring and treatment of disorders characterized by reduction in blood flow to the hand or foot such as atherosclerotic peripheral vascular disease or arteritis. The ambulatory skin temperature data can also be used in the monitoring and treatment of disorders characterized by decreased total cardiac output such as heart failure or shock as well as disorders characterized by constriction of blood vessels and increases in skin conductivity such as pain or stress.

The ambulatory monitor 10 micro-controller 24 is a very low power device with analog measurement and digital processing capabilities sufficient to: read the two temperature probes that sense ambient and skin surface temperatures; record and time-tag raw data in non-volatile flash memory that resides within the micro-controller chip; process the raw data to detect events; maintain a separate file of time-tagged events; manage the operating mode of the micro-controller 24 to reduce battery power consumption; and support the data interface by which data stored in micro-controller 24 memory is copied out to an external computer.

Software for the ambulatory monitor 10 can include programs for both the micro-controller 24 within the ambulatory monitor 10 as well as programs for the remote computer that reads the data gathered, stored, and transmitted by the micro-controller 24. A computer such as a PC or Palm Pilot with an off the shelf plotting software package can be used to extract data from the ARM micro-controller and present a convenient user interface for the physician.

The foregoing description illustrated an ambulatory monitor device that was designed for and operable in the fingertip area. The device can easily be adapted for use at other areas on the body depending on the application for which the monitor is gathering data. Specifically, the device can readily be adapted to fit about a patient's toe.

Moreover, the present invention has been described with respect to temperature sensors primarily. One of ordinary skill in the art can readily adapt the present invention to be used with sensors that perceive different data such as, for instance, pulse rate, blood pressure and the like.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An ambulatory skin temperature monitoring system comprising:
    a flexible band adapted to fit about the finger of a patient;
    a skin temperature sensor positioned to be in direct contact with the skin of the patient when said flexible band is attached to said patient;
    an ambient temperature sensor for determining the temperature of the environment about the patient;
    an electronics assembly integral with said flexible band wherein the electronics assembly comprises:
        a power source; and
        a micro-controller coupled with said skin temperature sensor and said ambient temperature sensor including a memory unit for storing temperature data obtained from said skin temperature sensor and said ambient temperature sensor.

2. The ambulatory skin temperature monitoring system of claim 1 wherein the flexible band includes an adhesive area for securing the flexible strap to the patient.

3. The ambulatory skin temperature monitoring system of claim 1 wherein said electronics assembly further comprises a skin conductivity sensor coupled with said micro-controller.

4. The ambulatory skin temperature monitoring system of claim 3 further comprising a data transport mechanism that facilitates the extraction of data from the micro-controller to a remote computing device.

5. The ambulatory skin temperature monitoring system of claim 4 wherein the data transport mechanism that facilitates the extraction of data from the micro-controller to a remote computing device comprises electrical contacts coupled with the micro-controller that are positioned to be accessible to a cable that can be connected to the remote computing device.

6. The ambulatory skin temperature monitoring system of claim 4 wherein the data transport mechanism that facilitates the extraction of data from the micro-controller to a remote computing device comprises a wireless transmitting device coupled with the micro-controller that can transmit data to the remote computing device.

7. An ambulatory skin temperature monitoring system comprising:
    a flexible band attachable on a patient;
    a skin temperature sensor positioned to be in direct contact with the skin of the patient when said flexible band is attached to said patient;
    an ambient temperature sensor for determining the temperature of the environment about the patient;
    an electronics assembly attached to said flexible band wherein the electronics assembly comprises:
        a power source;
        a micro-controller coupled with said skin temperature sensor and said ambient temperature sensor including a memo unit for storing temperature data obtained from said skin temperature sensor and said ambient temperature sensor; and
    a test/event button coupled with the micro-controller, said test/event button for permitting the patient to test whether the ambulatory skin temperature monitoring system has been properly affixed to the patient and is in an operational status.

8. The ambulatory skin temperature monitoring system of claim 7 further comprising a test/event button coupled with the micro-controller, said test/event button for permitting the patient to record the onset of suspected Raynaud's event.

9. The ambulatory skin temperature monitoring system of claim 8 further comprising an LED coupled with the micro-controller for indicating to the patient an acknowledgement of a depression of the test/event button.

10. An ambulatory skin temperature monitoring system comprising:
    a flexible band attachable on a patient;
    a skin temperature sensor positioned to be in direct contact with the skin of the patient when said flexible band is attached to said patient;
    an ambient temperature sensor for determining the temperature of the environment about the patient;
    an electronics assembly attached to said flexible band wherein the electronics assembly comprises:
        a power source;
        a micro-controller coupled with said skin temperature sensor and said ambient temperature sensor including a memory unit for storing temperature data obtained from said skin temperature sensor and said ambient temperature sensor; and
        a skin conductivity sensor couple with said micro-controller; and
    a data transport mechanism that facilitates the extraction of data from the micro-controller to a remote computing device; and
    a power readout button coupled with the micro-controller, said power readout button for powering the data transport mechanism.

11. An ambulatory skin temperature monitoring system comprising:
    means for measuring the skin temperature of the patient;
    means for measuring the ambient temperature near the patient; and
    means for storing temperature data obtained by said means for measuring the skin temperature and said means for measuring the ambient temperature near the patient; and
    means for attaching the ambulatory skin temperature monitoring system adapted to fit about the fingertip of a patient said means for measuring the skin temperature, said means for measuring the ambient temperature, and said means for storing temperature data being integral with said means for attaching the ambulatory skin temperature monitoring system.

12. The ambulatory skin temperature monitoring system of claim 11 wherein the means for attaching the ambulatory kin temperature monitoring system to a patient includes an adhesive area.

13. The ambulatory skin temperature monitoring system of claim 11 further comprising means for measuring the skin conductivity of the patient with respect to the ambulatory skin temperature monitoring stem.

14. The ambulatory skin temperature monitoring system of claim 13 further comprising means for transporting store data from the ambulatory skin temperature monitoring system to a remote computing device.

15. The ambulatory skin temperature monitoring system of claim 13 further comprising means for wirelessly transporting stored data from the ambulatory skin temperature monitoring system to a remote computing device.

16. An ambulatory skin temperature monitoring system comprising:
    means for measuring the skin temperature of the patient;
    means for measuring the ambient temperature near the patient;

means for storing temperature data obtained by said means for measuring the skin temperature and said means for measuring the ambient temperature near the patient;

means for attaching the ambulatory skin temperature monitoring system to a patient; and means for permitting the patient to test whether the ambulatory skin temperature monitoring system has been properly affixed to the patient and is in an operational status.

17. The ambulatory skin temperature monitoring system of claim 16 further comprising means for permitting the patient to record the onset of a suspected Raynaud's event.

18. The ambulatory skin temperature monitoring system of claim 17 further comprising means for indicating to the patient an acknowledgement of a depression of the test/event button.

19. An ambulatory monitoring system comprising:

a flexible band adapted to fit about the finger of a patient;

a sensor positioned to be in direct contact with the skin of the patient when said flexible band is attached to said patient;

an electronics assembly integral with said flexible band wherein the electronics assembly comprises:

a power source; and a micro-controller coupled with said sensor including a memory unit for storing sensor data obtained from said sensor.

20. The ambulatory monitoring system of claim 19 wherein said sensor is for detecting the pulse rate of the patient.

21. The ambulatory monitoring system of claim 19 wherein said sensor is for detecting the blood pressure of the patient.

22. The ambulatory monitoring system of claim 19 further comprising a data transport mechanism that facilitates the extraction of data from the micro-controller to a remote computing device.

23. The ambulatory monitoring system of claim 22 wherein the data transport mechanism that facilitates the extraction of data from the micro-controller to a remote computing device comprises electrical contacts coupled with the micro-controller that are positioned to be accessible to a cable that can be connected to the remote computing device.

24. The ambulatory monitoring system of claim 22 wherein the data transport mechanism that facilitates the extraction of data from the micro-controller to a remote computing device comprises a wireless transmitting device coupled with the micro-controller that can transmit data to the remote computing device.

* * * * *

UNITED STATES PATENT AND TRADEMARK OFFICE
CERTIFICATE OF CORRECTION

PATENT NO. : 6,847,913 B2
DATED : January 25, 2005
INVENTOR(S) : Fredrick M. Wigley et al.

It is certified that error appears in the above-identified patent and that said Letters Patent is hereby corrected as shown below:

Title page,
Item [75], Inventors, delete "Scott" and insert therefor -- Stott --

Column 5,
Line 56, delete "memo" and insert therefor -- memory --

Column 6,
Line 22, delete "couple" and insert therefor -- coupled --
Line 49, delete "kin" and insert therefor -- skin --
Line 56, delete "store" and insert therefor -- stored --

Signed and Sealed this

Twenty-fourth Day of May, 2005

JON W. DUDAS
*Director of the United States Patent and Trademark Office*